(12) United States Patent
Priester et al.

(10) Patent No.: US 7,027,239 B2
(45) Date of Patent: Apr. 11, 2006

(54) DATA ACQUISITION SYSTEM

(76) Inventors: William B. Priester, 8723 Windrush, Memphis, TN (US) 38125; Joseph H. Butler, Jr., 643 Brochardt Blvd., Knoxville, TN (US) 37922; Michael J. Twigg, 8715 Brucewood La., Knoxville, TN (US) 37923

( * ) Notice: Subject to any disclaimer, the term of this patent is extended or adjusted under 35 U.S.C. 154(b) by 491 days.

(21) Appl. No.: 10/098,018

(22) Filed: Mar. 13, 2002

(65) Prior Publication Data

US 2003/0137762 A1 Jul. 24, 2003

Related U.S. Application Data

(63) Continuation-in-part of application No. 10/008,293, filed on Dec. 3, 2001.

(51) Int. Cl.
*G11B 5/00* (2006.01)

(52) U.S. Cl. ............................................. 360/6; 360/32
(58) Field of Classification Search ................. 360/6, 360/32, 39, 46; 341/126, 155, 157; 704/270; 708/105, 108, 140; 369/1–4, 19, 20, 69, 70, 369/59.21, 59.24
See application file for complete search history.

(56) References Cited

U.S. PATENT DOCUMENTS

| | | | |
|---|---|---|---|
| 4,660,829 | A | 4/1987 | Whiteneir |
| 4,667,685 | A | 5/1987 | Fine |

(Continued)

FOREIGN PATENT DOCUMENTS

| | | |
|---|---|---|
| DE | 199 39 702 A | 2/2001 |
| DE | 101 04 669 A | 8/2002 |

OTHER PUBLICATIONS

Database WPI, Derwent Publications Ltd., London, GB; AN–2001–511053, XP002247163 & KR 2001 016 707 A (OH) Mar. 5, 2001, abstract.

Ziegler: "the soundcard used as an oszilloscope"; LINUX-NETMAG#4, Online!, Nov. 25, 1999, XP002247162 Retrived from the Internet: <URL:http://www.linxbetmag, com/en/issue4/m4oszillol.html>.

*Primary Examiner*—Alan T. Faber
(74) *Attorney, Agent, or Firm*—Luedeka, Neely & Graham, P.C.

(57) ABSTRACT

A data acquisition apparatus acquires an analog input signal from an analog sensor, and generates digital data based on the analog input signal for processing by a personal computing apparatus. The analog input signal generated by the analog sensor has a voltage component which varies according to a condition sensed by the analog sensor. The data acquisition apparatus includes a first conversion circuit, such as a voltage-to-frequency converter, coupled to the analog sensor which receives the analog input signal and generates an analog information transfer signal having a signal component which varies in relation to the voltage component of the analog input signal. A signal transfer device, such as a portable audio record/playback device, records the analog information transfer signal and transfers it to a first audio input of the personal computing apparatus. A second conversion circuit, such as a computer sound card in the personal computing apparatus, generates a digital information signal based upon the analog information transfer signal. A processor in the personal computing apparatus operates on the digital information signal to generate an information output signal based upon the signal component, where the information output signal varies in relation to the voltage component of the analog input signal. The processor preferably includes a frequency-to-voltage converter module for generating the information output signal based upon the frequency component of the analog information transfer signal.

21 Claims, 9 Drawing Sheets

U.S. PATENT DOCUMENTS

| | | |
|---|---|---|
| 5,027,688 A | 7/1991 | Suzuki et al. |
| 5,220,308 A | 6/1993 | Batzdorff et al. |
| 5,290,964 A | 3/1994 | Hiyoshi et al. |
| 5,310,679 A | 5/1994 | Artiss et al. |
| 5,324,038 A | 6/1994 | Sasser |
| 5,435,321 A | 7/1995 | McMillen et al. |
| 5,469,862 A | 11/1995 | Kovacevic |
| 5,474,088 A | 12/1995 | Zaharkin et al. |
| 5,509,809 A | 4/1996 | Clay |
| 5,586,943 A | 12/1996 | Clay |
| 5,704,846 A | 1/1998 | Johnson |
| 5,754,121 A | 5/1998 | Ward et al. |
| 5,823,886 A | 10/1998 | Murray |
| 6,546,516 B1 * | 4/2003 | Wright et al. .............. 714/762 |

* cited by examiner

DATA ACQUISITION SYSTEM

This application is a continuation-in-part of U.S. patent application Ser. No. 10/008,293 which was filed on Dec. 3, 2001.

FIELD

This invention relates to a data acquisition system. More particularly, the invention relates to a system for acquiring data using a sound card of a personal computer.

BACKGROUND

Generally, data acquisition involves interfacing an analog sensor with a recording or display device to measure and record some value of interest over a period of time. For example, a meteorologist may want to measure and record the temperature during a 24-hour period. Sensors outputs are usually analog in nature, with voltage as the common output medium. The meteorologist's thermocouple, for example, may output 5.1 volts when the temperature is 70° F., and 5.4 volts when the temperature is 80° F. Before the advent of computers, this type of data was recorded continuously on a strip chart.

With the advent of low cost digital computers, almost all data storage is now done digitally. Typical commercially-available data acquisition systems sample the voltage signal from a sensor in discrete time intervals, e.g., once every minute. Generally, this analog voltage must be converted to a digital signal that the computer can process and store. This analog-to-digital conversion is typically done with specialized data acquisition hardware and software which must be installed in a user's computer. Generally, such data acquisition packages are expensive, timing consuming to install, require specialized knowledge to setup, and are not easily transferable from one computer to another.

What is needed, therefore, is a data acquisition system which is inexpensive, simple to setup and use, and easily transferable from one computer to another.

SUMMARY

The above and other needs are met by a data acquisition apparatus for acquiring an analog input signal from an analog sensor, and generating digital data based thereon for processing by a personal computing apparatus, where the analog input signal has a voltage component which varies according to a condition sensed by the analog sensor. The data acquisition apparatus includes a first conversion circuit, a signal transfer device, a second conversion circuit, and a processor.

The first conversion circuit, which is coupled to the analog sensor, receives the analog input signal and generates an analog information transfer signal having a signal component which varies in relation to the voltage component of the analog input signal. In preferred embodiments of the invention, the first conversion circuit comprises a voltage-to-frequency converter which generates the analog information transfer signal having a frequency component which varies in relation to the voltage component of the analog input signal.

The signal transfer device transfers the analog information transfer signal to a first audio input of the personal computing apparatus. In a most preferred embodiment, the signal transfer device comprises an audio record/playback device which may be coupled to the first conversion circuit for receiving and recording the analog information transfer signal on a first audio channel. The audio record/playback device of this embodiment is also operable to be coupled to the first audio input of the personal computing apparatus for transferring the analog information transfer signal from the first audio channel to the first analog input of the personal computing apparatus.

The second conversion circuit, which is coupled to the first audio input of the personal computing apparatus, generates a digital information signal based upon the analog information transfer signal. In a preferred embodiment, the second conversion circuit comprises a sound card associated with the personal computing apparatus.

The processor, which is associated with the personal computing apparatus, operates on the digital information signal to generate an information output signal which varies in relation to the voltage component of the analog input signal. The processor preferably includes a frequency-to-voltage converter module for operating on the digital information signal to generate the information output signal based upon the frequency component of the analog information transfer signal.

Thus, the data acquisition apparatus of the preferred embodiment overcomes the drawbacks of prior systems by incorporating a voltage-to-frequency converter to convert the sensor voltage signal into a frequency signal. Converting the sensor voltage signal into a frequency signal prior to sampling allows measurement of sensor signals having a direct current (DC) component. Further, by incorporating a standard personal computer sound card as the analog-to-digital conversion circuit, the preferred embodiment of the invention provides an inexpensive alternative to the cost-prohibitive data acquisition boards of the prior art.

Some preferred embodiments of the invention include a microphone which is electrically coupled to a second audio channel of the audio record/playback device for generating an audio input signal. The audio record/playback device preferably records the audio input signal from the microphone on a second audio channel. The second audio channel of the audio record/playback device is coupled to a second audio input of the personal computing apparatus for transferring the audio input signal from the second audio channel to the second audio input of the personal computing apparatus.

In another aspect, the invention provides a method for acquiring information from one or more analog sources and transferring the information to a personal computing apparatus. The method includes receiving an analog input signal from an analog source, where the analog input signal has a voltage component which varies according to the information. An analog information transfer signal is generated which has a signal component varying in relation to the voltage component of the analog input signal. The analog information transfer signal is transferred to a first analog audio input of the personal computing apparatus, and a digital information signal is generated based upon the analog information transfer signal having the signal component. The method also includes operating on the digital information signal to generate an information output signal based upon the signal component, such that the information output signal varies in relation to the voltage component of the analog input signal.

BRIEF DESCRIPTION OF THE DRAWINGS

Further advantages of the invention are apparent by reference to the detailed description when considered in conjunction with the figures, which are not to scale so as to more clearly show the details, wherein like reference numbers indicate like elements throughout the several views, and wherein.

DETAILED DESCRIPTION

Figure 1:
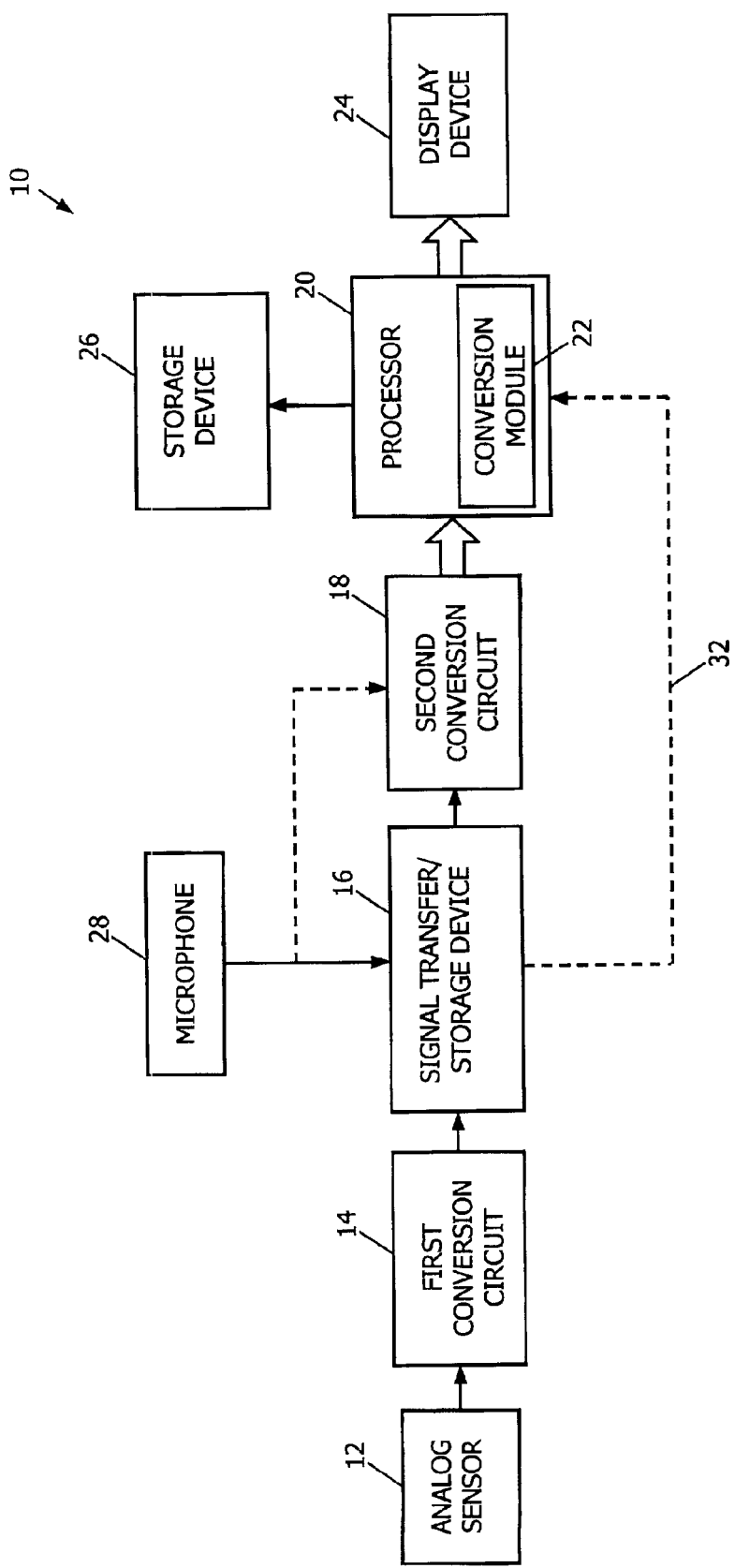
FIG. 1 depicts a functional block diagram of a data acquisition system according to a preferred embodiment of the invention.

Referring now to FIG. 1, there is generally depicted a preferred embodiment of a data acquisition and storage system 10. The system 10 preferably includes an analog sensor 12 which generates an analog input signal based on some sensed physical condition. The analog input signal has a signal component, such as a voltage component, which varies according to the sensed condition. The system 10 includes a first conversion circuit 14 which generates an analog information transfer signal based on the analog input signal, and a signal transfer/storage device 16 for transferring the analog information transfer signal to a second conversion circuit 18. The second conversion circuit 18 generates a digital information signal based upon the analog information transfer signal. The system 10 also preferably includes a processor 20, the operation of which is preferably controlled by execution of a conversion module 22. Under control of the conversion module 22, the processor 20 operates on the digital information signal to generate an information output signal based upon the signal component of the analog input signal. The information output signal is provided to an output device 24 which translates the information output signal into a format which may be perceived by a human operator.

Preferred embodiments of the system 10 include a microphone 28 for generating an audio input signal, such as a voice comment or annotation, which is related in time to the analog input signal. The microphone 28 and its preferred uses are also described in more detail below.

Figure 4A:
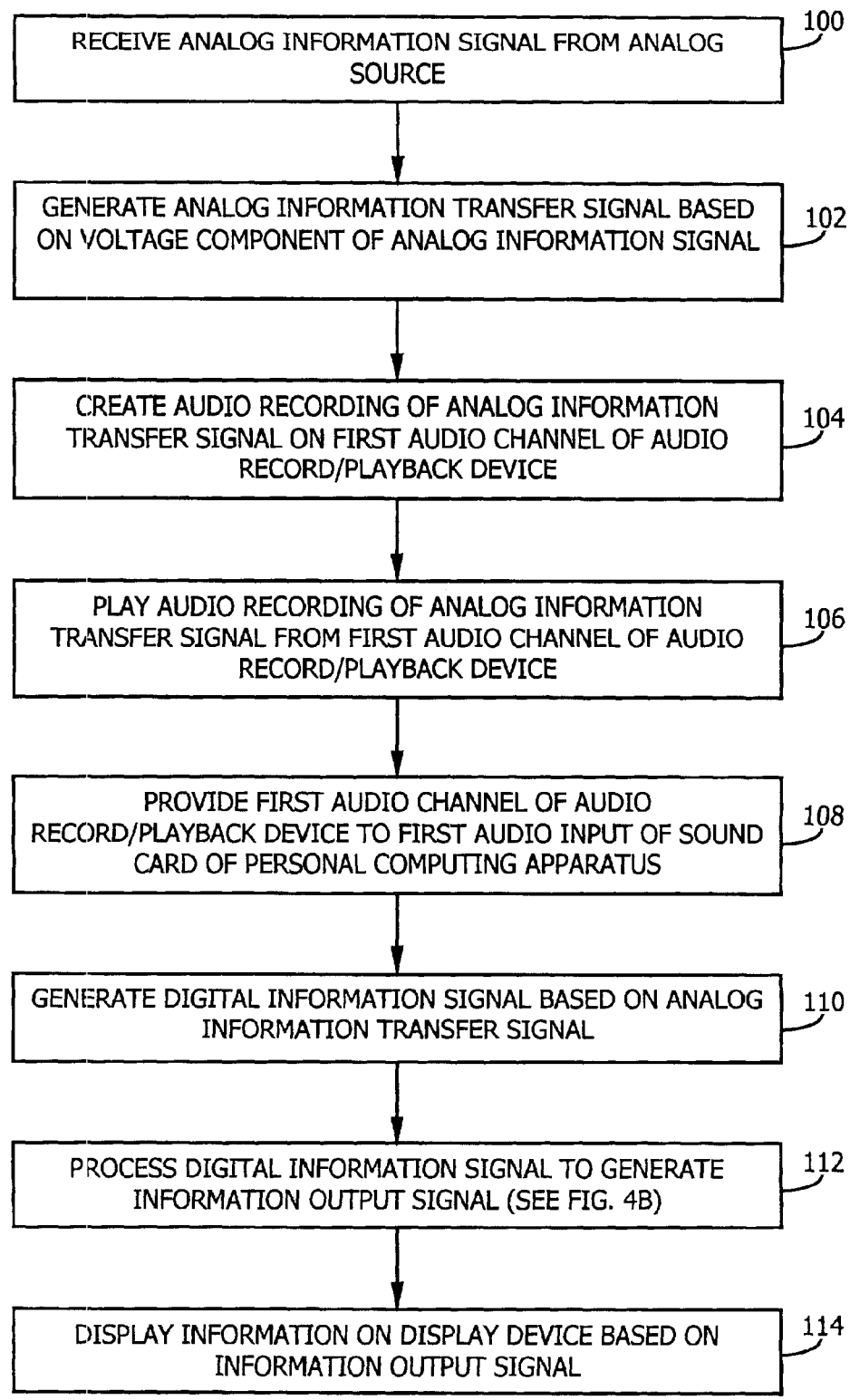
FIGS. 4A and 4B depict a functional flow diagram of a method for acquiring information from an analog source and transferring the information to a personal computing apparatus according to a preferred embodiment of the invention.

Further description of each of the components depicted in FIG. 1 is provided hereinafter. The preferred process steps performed by the system 10 are depicted in the flow diagrams of FIGS. 4A, 4B, and 5.

In preferred embodiments of the invention, the analog sensor 12 is a device which generates a voltage signal having a component, such as amplitude, that varies in relation to some sensed parameter. For example, in one embodiment, the sensor 12 is an angle sensor such as is described in the copending patent application Ser. No. 10/008,293. In alternative embodiments, the sensor 12 is a temperature sensor, pressure sensor, vibration sensor, or other type sensing device. Thus, it should be appreciated that the invention is not limited to any particular type of sensor 12.

Figure 2:
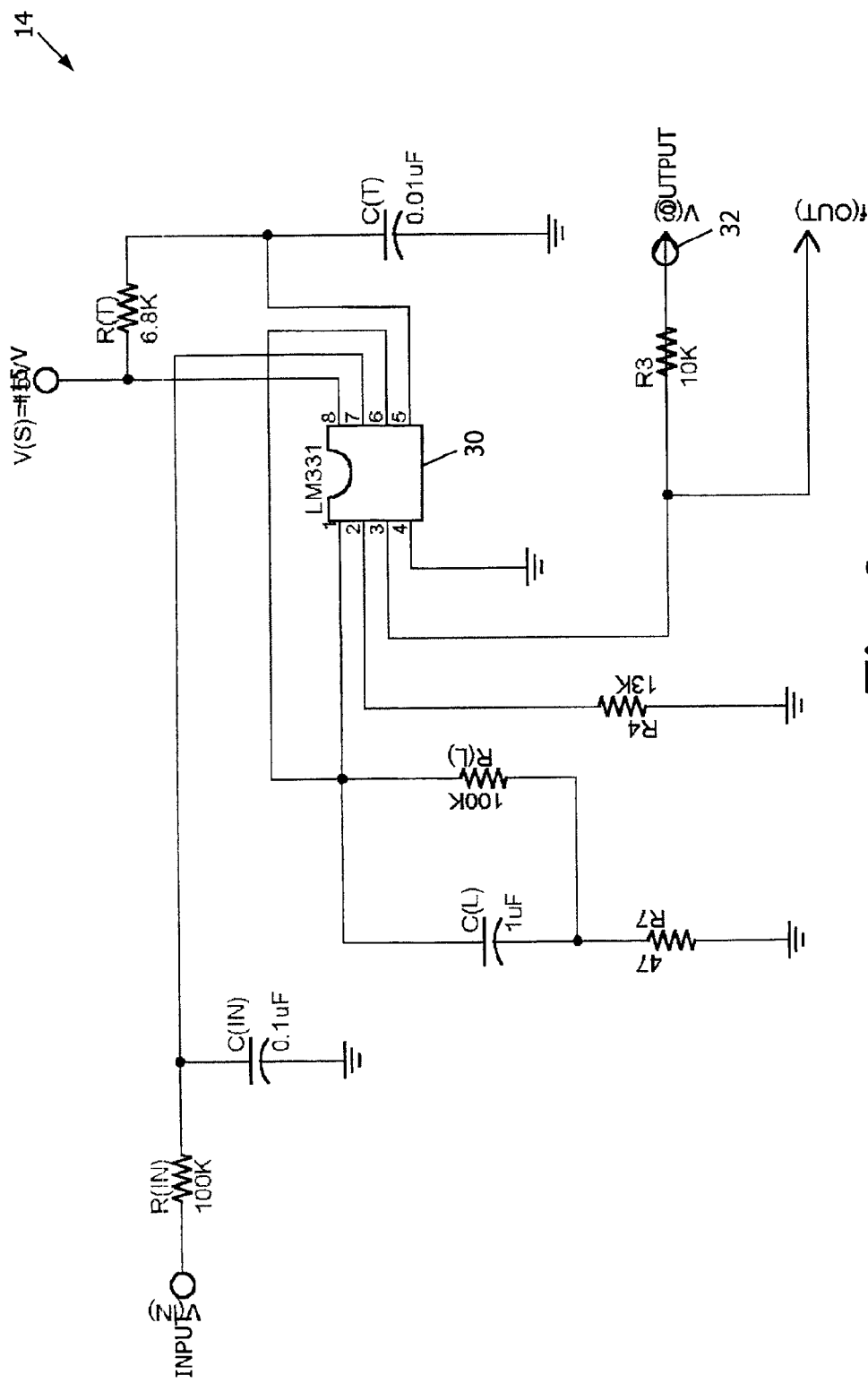
FIG. 2 depicts a voltage-to-frequency conversion circuit according to a preferred embodiment of the invention.
Figure 3:
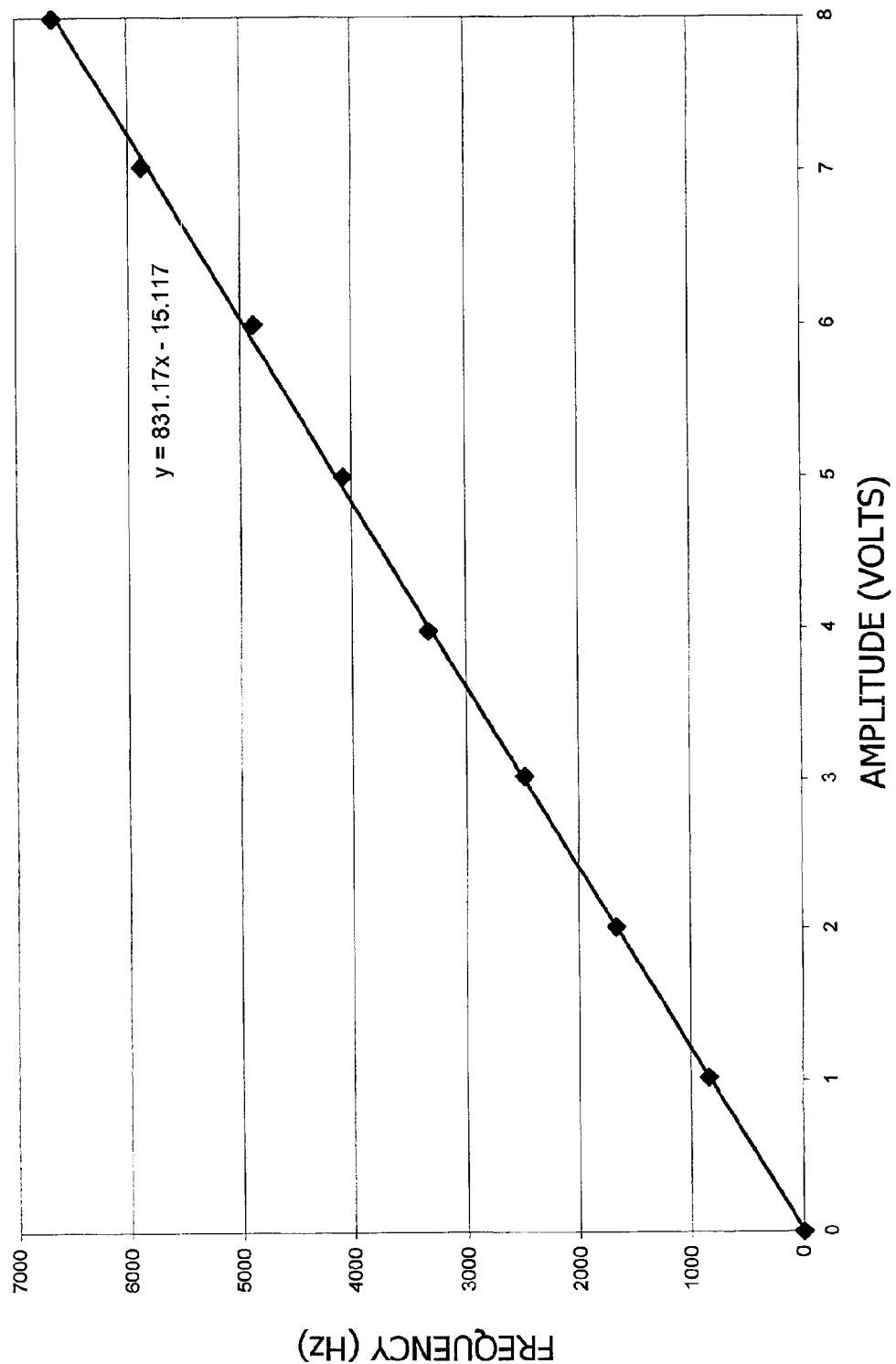
FIG. 3 depicts a voltage-to-frequency function provided by the voltage-to-frequency conversion circuit of the preferred embodiment of the invention.

Preferably, the first conversion circuit 14 is a voltage-to-frequency converter, such as depicted in the schematic diagram of FIG. 2. In the embodiment depicted in FIG. 2, the first conversion circuit 14 incorporates a voltage-to-frequency converter device 30, such as an integrated circuit device having model number LM231/LM331 manufactured by National Semiconductor. The device 30 receives the analog input signal from the sensor 12 at pin 7 (step 100 in FIG. 4A) and provides an output signal at pin 3 having a frequency component which is proportionally related to the amplitude of the analog input signal (step 102). FIG. 3 depicts an example of the voltage-to-frequency relationship between the amplitude of the source signal from the sensor 12 and the frequency of the output signal as provided by the preferred embodiment of the first conversion circuit 14. The output signal generated by the first conversion circuit 14 is also referred to herein as an analog information transfer signal. Preferably, the circuit 14 includes an output connector 32, such as a standard audio connector, for coupling the analog information transfer signal to the signal transfer/storage device 16.

It should be appreciated that the conversion circuit 14 depicted in FIG. 2 is one example of a circuit for generating an analog information transfer signal having a frequency component which varies in relation to an amplitude component of an input signal. However, it should be appreciated that the invention is not limited to any particular configuration of the first conversion circuit 14. It should also be appreciated that the invention is not limited to generating an analog information transfer signal having a frequency component varying in relation to the amplitude of the analog input signal. In an alternative embodiment of the invention, the analog information transfer signal is generated to have an amplitude component which varies in relation to the amplitude of the analog input signal.

In a preferred embodiment of the invention, the signal transfer/storage device 16 is a portable personal audio record/playback device, such as an audio cassette tape recorder, or a portable digital audio recording device, such as an MP3 recorder/player. Preferably, an input connector, such as a line input or microphone input, of the signal transfer/storage device 16 is coupled to the output connector 32 of the first conversion circuit 14 by way of an audio cable. In this manner, the analog information transfer signal is coupled from the first conversion circuit 14 to an audio channel of the signal transfer/storage device 16 where the signal is recorded (step 104). In the embodiment wherein the signal transfer/storage device 16 is an audio cassette tape recorder, the analog information transfer signal is recorded on the magnetic tape of an audio cassette. In the embodiment wherein the signal transfer/storage device 16 is a portable digital audio recording device, the analog information transfer signal is recorded in a digital format in semiconductor memory or on a magnetic or optical disk within the device 16.

The second conversion circuit 18 is preferably an analog-to-digital conversion device for converting the analog information transfer signal into a digital information signal. In the preferred embodiment of the invention, the second conversion circuit 18 comprises a sound card, such as is typically provided in all commercially-available personal computers. For example, in one embodiment the second conversion circuit 18 is a Sound Blaster AWE-32 sound card manufactured by Creative Labs. The typical sampling rate for such a sound card is about 22,050 Hz.

Preferably, an input connector on the second conversion circuit 18, such as a line input or microphone input, is coupled to an output connector on the signal transfer/storage device 16 by way of an audio cable. In this manner, when the recorded analog information transfer signal is "played back" on the signal transfer/storage device 16 (step 106), the analog information transfer signal is coupled from the signal transfer/storage device 16 to the second conversion circuit 18 (step 108). As discussed above, the second conversion circuit 18 converts the analog information transfer signal into the digital information signal which may be processed by the processor 20 (step 110).

Figure 6:
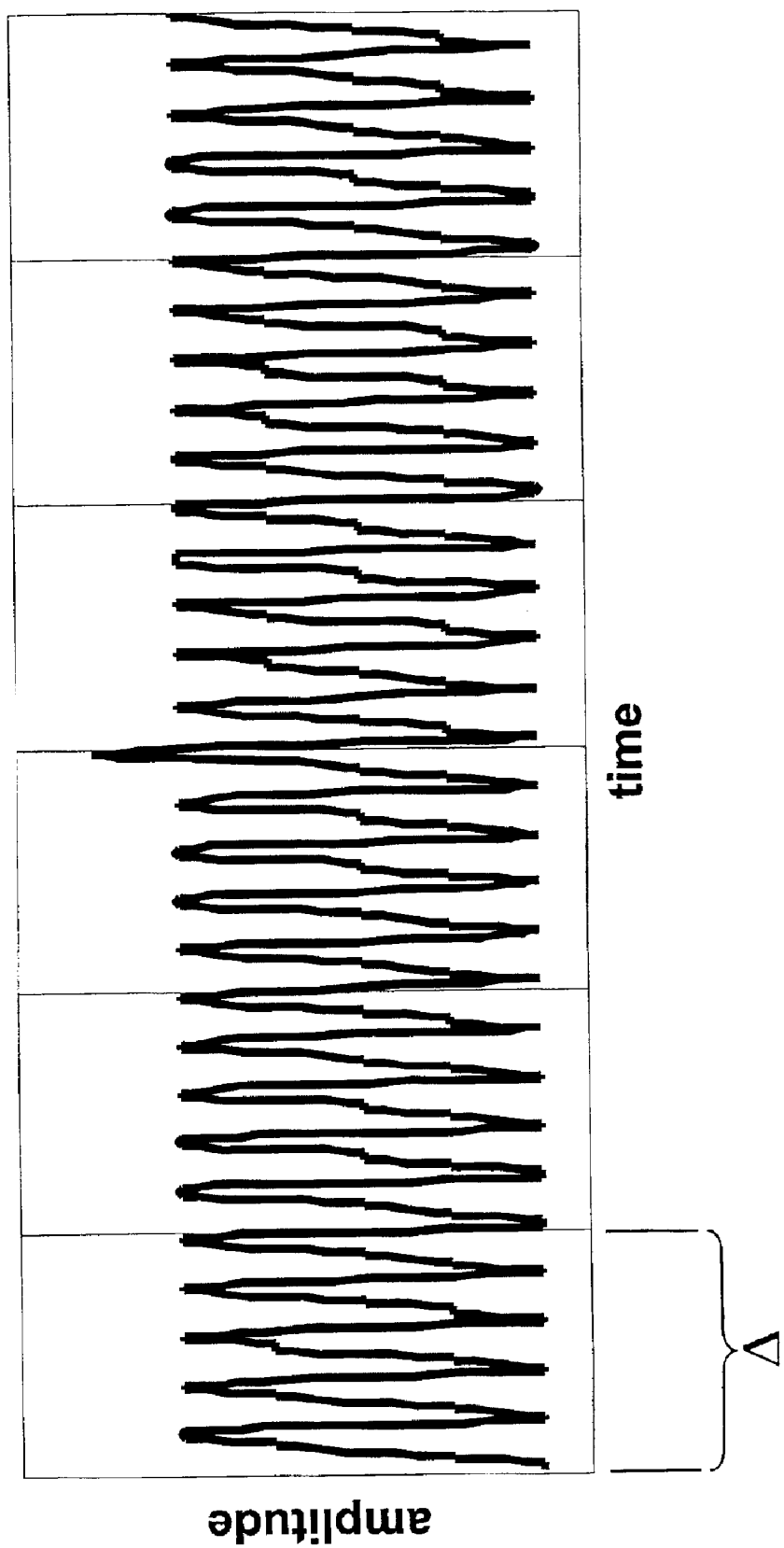
FIG. 6 depicts a time-domain plot of an analog information transfer signal according to a preferred embodiment of the invention.

In the preferred embodiment of the invention, the sensor information contained in the digital information signal is extracted by a frequency-to-voltage conversion module 22 executed by the processor 20 (step 112). Preferably, the module 22 extracts the sensor information according to the process steps depicted in FIG. 4B. At step 116, the module 22 breaks the digital information signal down into discrete segments of Δ number of samples, as depicted in FIG. 6. Preferably, Δ is a factor of 2, i.e. $\Delta=2^N$, where N is an integer. A smaller value of Δ results in a finer output resolution, but may result in aliasing problems if it is too small.

Figure 4B:
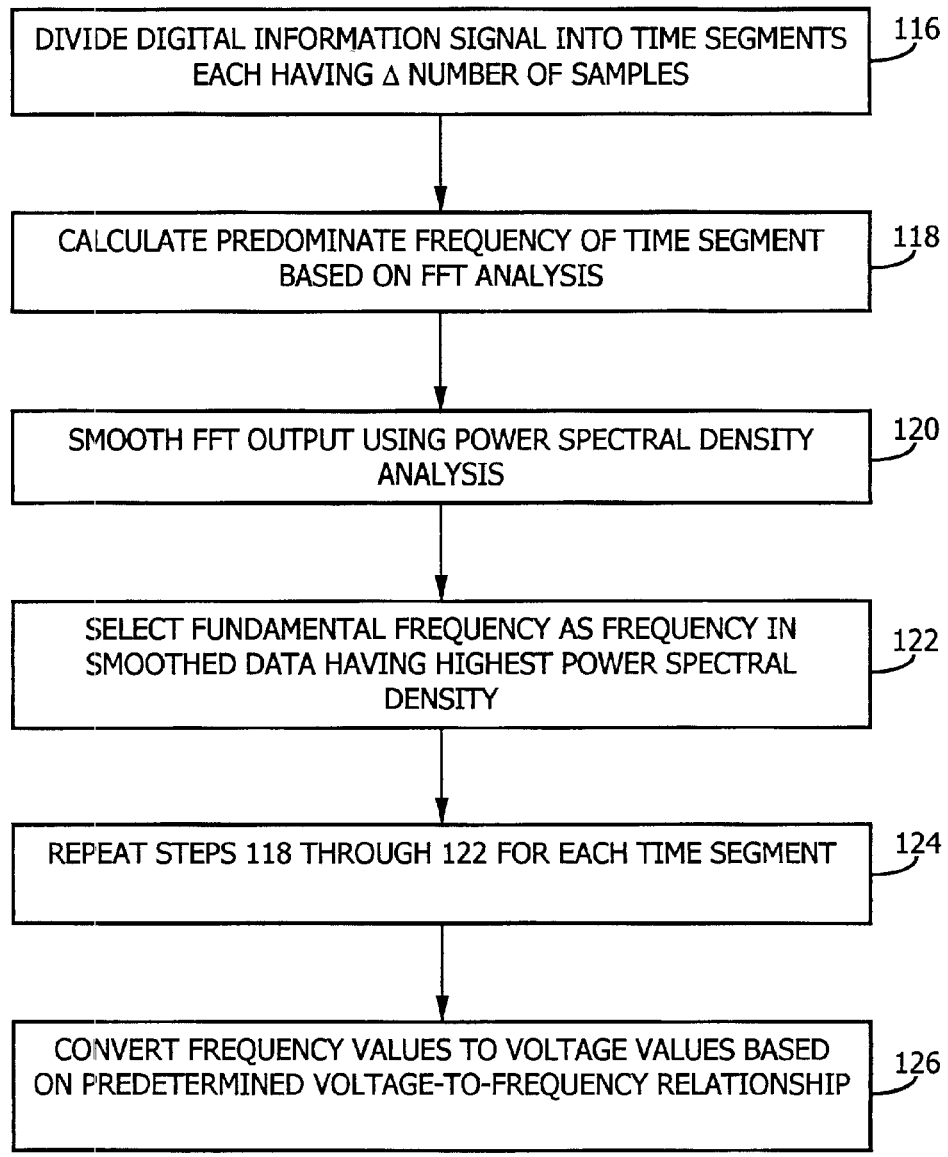
Figure 5:
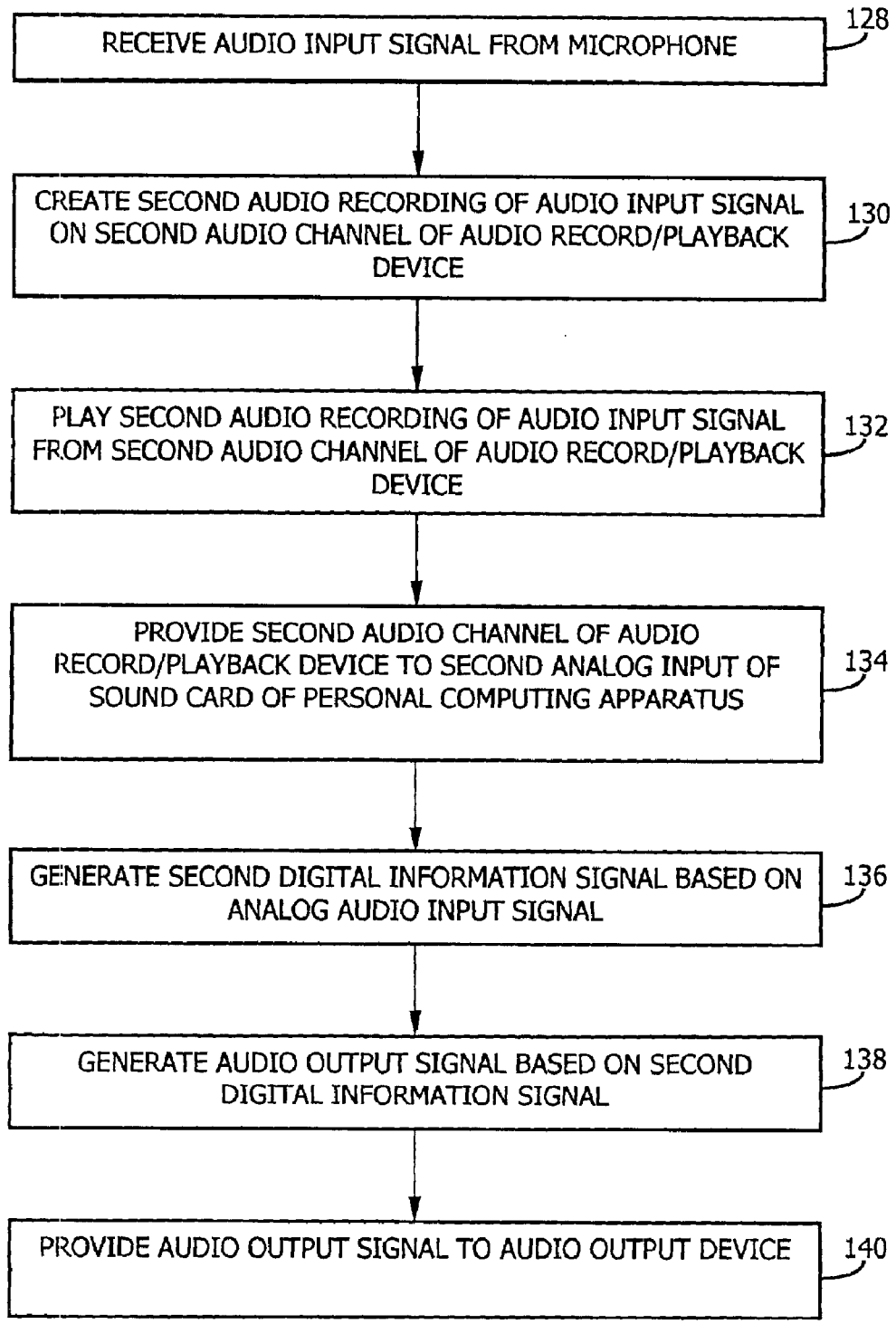
FIG. 5 depicts a functional flow diagram of a method for acquiring and transferring an audio input signal according to a preferred embodiment of the invention.

At step 118 of FIG. 4B, the module 22 calculates the predominate frequency in each of the time segments. In the preferred embodiment, this step is performed by fast Fourier transform (FFT) analysis using a Visual Basic subroutine FFT.BAS from a ProMath software package produced by Tera Tech. A typical plot of the frequency versus amplitude function generated by the FFT analysis is shown in FIG. 7.

Figure 7:
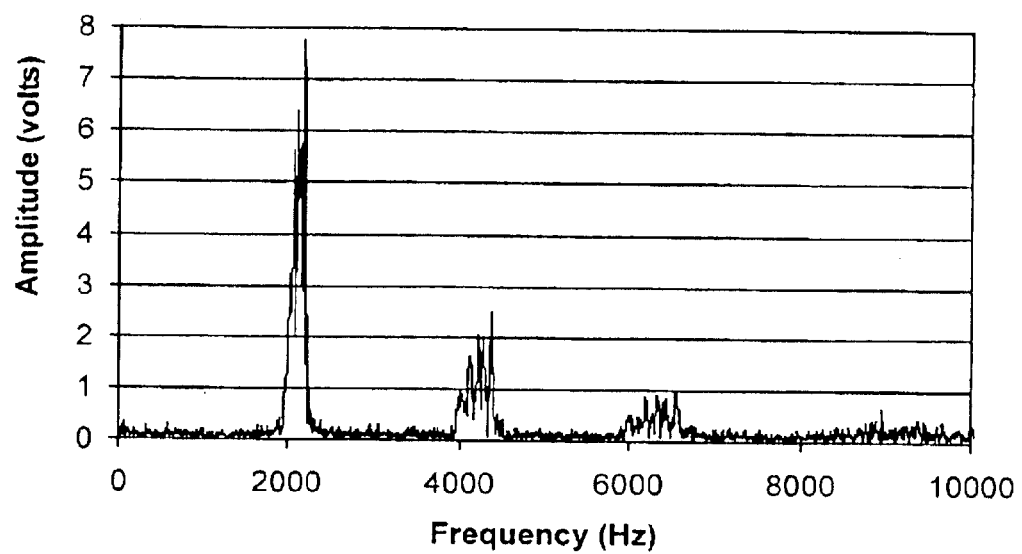
FIGS. 7 and 8 depict frequency-domain plots of an analog information transfer signal during a particular time segment according to a preferred embodiment of the invention.
Figure 8:
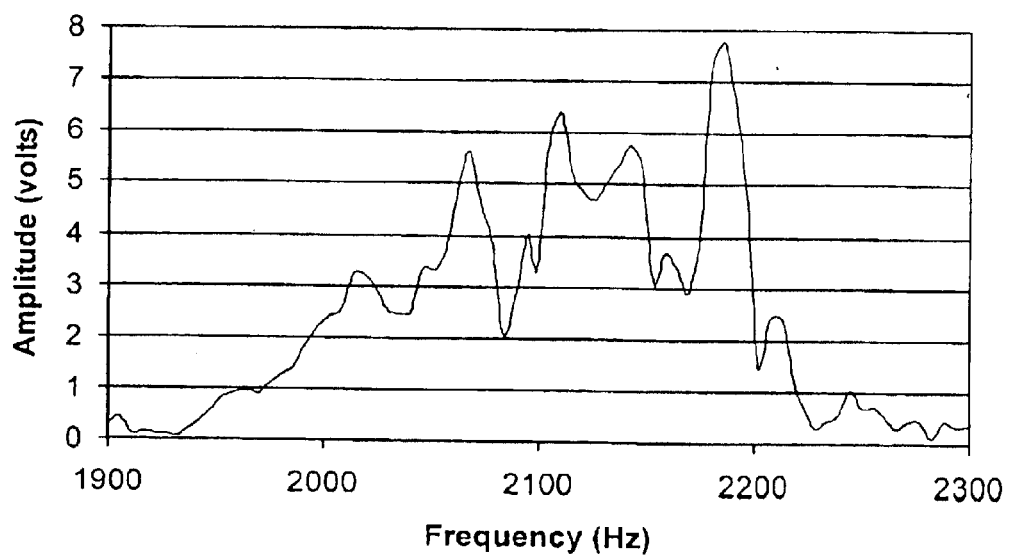
Figure 9:
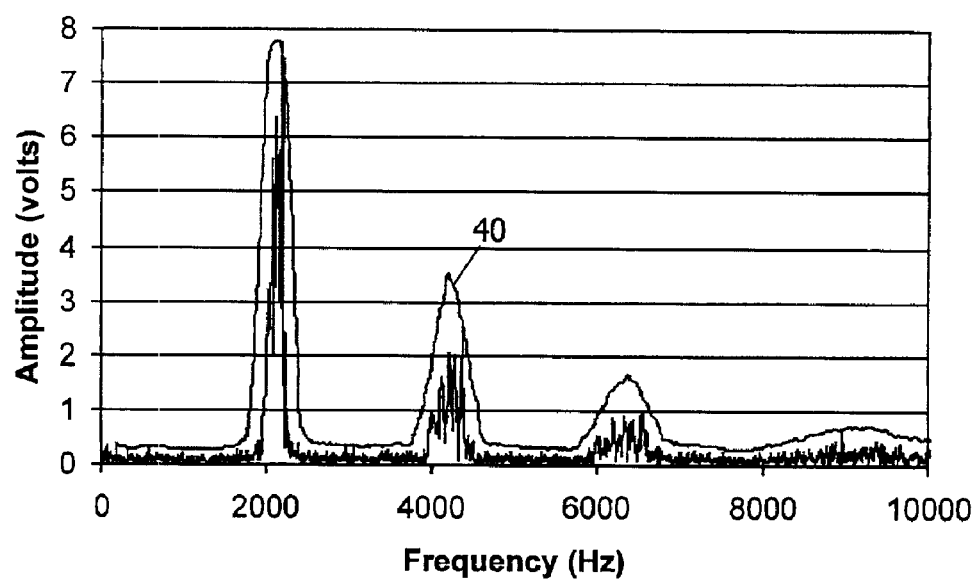
FIGS. 9 and 10 depict smoothed frequency-domain plots of the power spectral density of an analog information transfer signal during a particular time segment according to a preferred embodiment of the invention.
Figure 10:
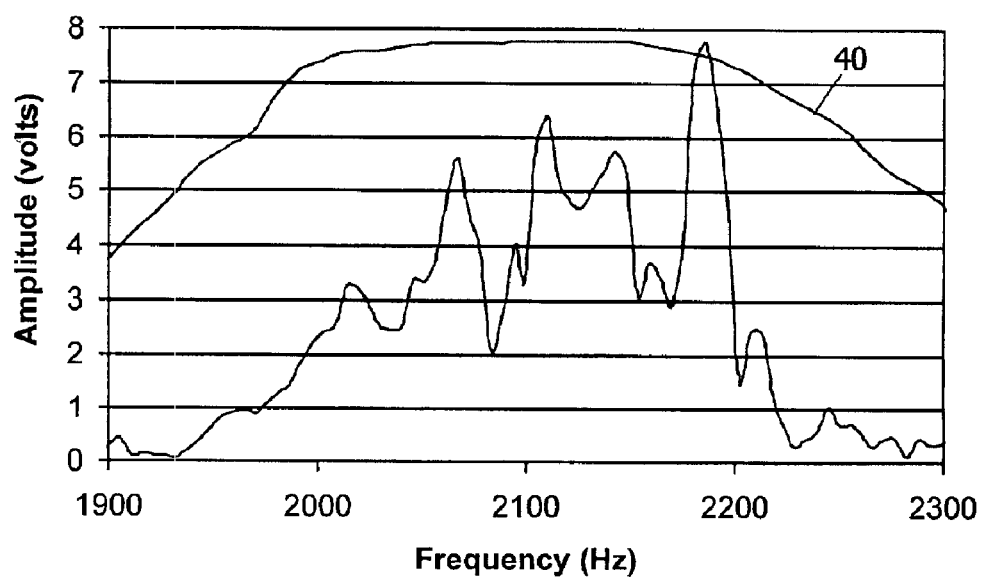

In the example depicted in FIG. 7, the dominate frequency is apparently about 2100 Hz. However, as depicted in the higher-resolution view of FIG. 8, picking the dominate frequency amid all the noise in the FFT output is not as simple as choosing the highest amplitude. Rather, according to the method of the present invention, the module 22 smoothes out the noise in the FFT output data by calculating the power spectral density (PSD) at each discrete frequency in the FFT output data (step 120). This is preferably accomplished using a sliding window wherein the amplitude values of x number of data points centered about each frequency are summed. These sum values are preferably scaled, resulting in the smoothed curve 40 shown in FIGS. 9 and 10. In the preferred embodiment, the module 22 selects the fundamental frequency as the frequency in the smoothed data having the highest PSD (step 122). Based on the smoothed curves shown in FIGS. 9 and 10, the fundamental frequency of the sample data set is about 2132 Hz.

The module 22 preferably repeats steps 118 through 122 for each time segment to provide a data set of frequency versus time (step 124). In the preferred embodiment, the frequency values in the frequency versus time data are then converted to voltage values using a voltage-to-frequency relationship, such as the linear relationship depicted in FIG. 3 (step 126). The voltage versus time data, which represents the information sensed by the sensor 12, is then provided to a display device 24, such as a video card and computer monitor associated with the processor 20, where the data is displayed (step 114 in FIG. 4A). For example, the data may be displayed in a continuously updated "strip chart" format on the display device 24. Of course, the data may also be stored on a storage device 26, such as a magnetic or optical disc drive associated with the processor 20 (See FIG. 1).

As depicted in FIG. 1, the preferred embodiment of the data acquisition system 10 includes an audio source, such as the microphone 28, for generating an audio input signal based on spoken comments. For example, if the system 10 is used to acquire joint angle data, as described in copending U.S. patent application Ser. No. 10/008,293, a user of the system 10 may make voice comments into the microphone 28 regarding the particular action which is taking place at the time of the joint angle data acquisition.

Preferably, the signal transfer/storage device 16 receives the audio input signal from the microphone 28 (step 128 in FIG. 5), and transfers the audio input signal to a second audio channel input of the second conversion circuit 18. In the preferred embodiment described above, the signal transfer/storage device 16 is a portable personal audio record/playback device, such as an audio cassette tape recorder, or a portable digital audio recording device, such as an MP3 recorder/player. The microphone 28 is preferably coupled to a microphone input of the signal transfer/storage device 16. In the embodiment wherein the signal transfer/storage device 16 is an audio cassette tape recorder, the audio input signal from the microphone 28 is recorded on a second audio channel of an audio cassette tape. In the embodiment wherein the signal transfer/storage device 16 is a portable digital audio recording device, the audio input signal is recorded in a second channel in a digital format in semiconductor memory or on a magnetic or optical disk within the device 16. Thus, in this embodiment, the information from the sensor 12 is recorded on one channel of the device 16, such as a left stereo channel, and the voice information from the microphone 28 is simultaneously recorded on a second channel of the device 16, such as a right stereo channel.

Typically, a commercially-available cassette tape recorder/player includes a single miniature stereo microphone input jack for receiving left and right channel microphone signals. When such a recorder/player is implemented as the transfer/storage device 16, an audio Y-adapter (such as Radio Shack part number 274-375) may be used to split the two input channels into two separate audio input jacks. In this case, the microphone 28 plugs into one of the two input jacks of the adapter, and the analog information transfer signal from the first conversion circuit 14 is provided to the other input jack of the adapter.

It should be appreciated that the invention is not limited to any particular number of data transfer channels. For example, in the embodiment of the invention wherein the signal transfer/storage device 16 is an audio cassette tape recorder, a first sensor signal, such as from a temperature sensor, may be recorded on the left audio channel of an audio cassette tape, and a second sensor signal, such as from a pressure sensor, may be recorded on the right audio channel of the same audio cassette tape. However, the scope of the invention encompasses any number of data transfer channels provided by the device 16.

In an alternative embodiment of the invention, the transfer/storage device 16 is an audio cable which couples the analog information transfer signal directly from the first conversion circuit 14 to the second conversion circuit 18. This embodiment may be particularly useful in situations wherein the analog sensor 12 and the first conversion circuit 14 are at fixed locations relative to the second conversion circuit 18 and the processor 20. For example, the analog sensor 12 may be a temperature sensor located outside a building for sensing the outside air temperature, and the second conversion circuit 18 and the processor 20, located inside the building, are used to log the temperature signal.

As discussed above, in one embodiment of the invention, the signal transfer/storage device 16 comprises a portable digital audio recording device, such as an MP3 recorder/player. In this embodiment, the second conversion circuit 18 comprises an analog-to-digital converter circuit within the portable digital audio recording device. Thus, in this embodiment, the analog information transfer signal is converted into a digital information signal, such as using the MP3 or similar encoding scheme, and is stored in digital format in semiconductor memory or on a magnetic or optical disk within the portable digital audio recording device. Preferably, the portable digital audio recording device of this embodiment includes a digital interface port, such as a Universal Serial Bus (USB) port, which may be coupled to a corresponding digital interface port associated with the processor 20. In this manner, the digital information signal stored in the portable digital audio recording device may be transferred from the storage device within the portable digital audio recording device directly to the processor 20. Once the digital information signal is provided to the processor 20, the conversion module 22 preferably operates on the digital information signal in the manner described above to extract the sensor information.

The foregoing description of preferred embodiments for this invention have been presented for purposes of illustration and description. They are not intended to be exhaustive or to limit the invention to the precise form disclosed. Obvious modifications or variations are possible in light of the above teachings. The embodiments are chosen and described in an effort to provide the best illustrations of the principles of the invention and its practical application, and to thereby enable one of ordinary skill in the art to utilize the invention in various embodiments and with various modifications as is suited to the particular use contemplated. All such modifications and variations are within the scope of the invention as determined by the appended claims when interpreted in accordance with the breadth to which they are fairly, legally, and equitably entitled.

What is claimed is:

1. A method for acquiring information from one or more analog sources and transferring the information to a personal computing apparatus, comprising:
    (a) receiving an analog input signal from an analog source, the analog input signal having a voltage component which varies according to the information;
    (b) generating an analog information transfer signal having a frequency component which varies in relation to the voltage component of the analog input signal;
    (c) transferring the analog information transfer signal to a first analog audio input of the personal computing apparatus;
    (d) generating a digital information signal based upon the analog information transfer signal having the signal component; and
    (e) operating on the digital information signal to generate the information output signal based upon the frequency component, the information output signal thereby varying in relation to the voltage component of the analog input signal.

2. The method of claim 1 wherein step (c) further comprises transferring the analog information transfer signal directly to the first analog input of the personal computing apparatus via one or more electrical conductors.

3. The method of claim 1 wherein:
    step (c) further comprises transferring the analog information transfer signal to a first audio input of a sound card associated with the personal computing apparatus; and
    step (d) further comprises using the sound card to generate the digital information signal based upon the first analog information transfer signal.

4. The method of claim 1 further comprising:
    (f) receiving an audio input signal from an audio source;
    (g) transferring the audio input signal to a second analog input of the personal computing apparatus;
    (h) generating a second digital information signal based upon the audio input signal;
    (i) generating an audio output signal based second digital information signal;
    (j) providing the audio output signal to an audio output device.

5. A method for acquiring information from one or more analog sources and transferring the information to a personal computing apparatus, comprising:
    (a) receiving an analog input signal from an analog source, the analog input signal having a voltage component which varies according to the information;
    (b) generating an analog information transfer signal having a signal component which varies in relation to the voltage component of the analog input signal;
    (c) creating a first audio recording of the analog information transfer signal on a first audio channel of an audio record/playback device;
    (d) playing the first audio recording on the first audio channel using the audio record/playback device; and
    (e) providing the first audio channel of the audio record/playback device to the first analog input of the personal computing apparatus while performing step (d).

6. The method of claim 5 wherein:
    step (c) further comprises creating the first audio recording of the analog information transfer signal on the first audio channel of an audio cassette tape recorder;
    step (d) further comprises playing the first audio recording on the first audio channel using the audio cassette tape recorder; and
    step (e) further comprises providing the first audio channel of the audio cassette tape recorder to the first analog input of the personal computing apparatus while performing step (d).

7. The method of claim 5 wherein:
    step (c) further comprises creating the first audio recording of the analog information transfer signal on the first audio channel of a digital audio recording device;
    step (d) further comprises playing the first audio recording on the first audio channel using the digital audio recording device; and
    step (e) further comprises providing the first audio channel of the digital audio recording device to the first analog input of the personal computing apparatus while performing step (d).

8. A method for acquiring information from one or more analog sources and transferring the information to a personal computing apparatus, comprising:
    (a) receiving an analog input signal from an analog input source, the analog input signal having a voltage component which varies according to the information;
    (b) generating an analog information transfer signal having a signal component which varies in relation to the voltage component of the analog input signal;

(c) transferring the analog information transfer signal to a first analog audio input of the personal computing apparatus;

(d) generating a digital information signal based upon the analog information transfer signal having the signal component;

(e) operating on the digital information signal to generate an information output signal based upon the signal component, the information output signal thereby varying in relation to the voltage component of the analog input signal;

(f) receiving an audio input signal from an audio source;

(g) creating a second audio recording of the audio input signal on a second audio channel of an audio record/playback device;

(h) playing the second audio recording on the second audio channel using the audio record/playback device;

(i) providing the second audio channel of the audio record/playback device to a second analog input of the personal computing apparatus while performing step (h);

(j) generating a second digital information signal based upon the audio input signal;

(k) generating an audio output signal based second digital information signal; and (l) providing the audio output signal to an audio output device.

9. The method of claim 8 wherein:

step (i) further comprises providing the second audio channel of the audio record/playback device to a second audio input of a sound card associated with the personal computing apparatus; and step (j) further comprises using the sound card to generate the second digital information signal based upon the analog audio input signal.

10. A method for acquiring information from one or more analog sources and transferring the information to a personal computing apparatus, comprising:

(a) receiving an analog input signal from an analog source, the analog input signal having a voltage component which varies according to the information;

(b) generating an analog information transfer signal having a frequency component which varies in relation to the voltage component of the analog input signal;

(c) creating a first audio recording of the analog information transfer signal on a first audio channel of an audio record/playback device;

(d) playing the first audio recording on the first audio channel using the audio record/playback device; and (e) providing the first audio channel of the audio record/playback device to a first audio input of a sound card associated with the personal computing apparatus while performing step (d);

(f) using the sound card to generate a digital information signal based upon the analog information transfer signal having the signal component; and (g) operating on the digital information signal to generate an information output signal based upon the frequency component, the information output signal thereby varying in relation to the voltage component of the analog input signal.

11. The method of claim 10 further comprising:

(h) receiving an audio input signal from an audio source;

(i) creating a second audio recording of the audio input signal on a second audio channel of the audio record/playback device;

(j) playing the second audio recording on the second audio channel using the audio record/playback device; and (k) providing the second audio channel of the audio record/playback device to a second audio input of the sound card while performing step (j);

(l) generating a second digital information signal based upon the audio input signal;

(m) generating an audio output signal based on the second digital information signal; and (n) providing the audio output signal to an audio output device.

12. A data acquisition apparatus for acquiring an analog sensor signal from an analog sensor, and for generating digital data based on the analog sensor signal for processing by a personal computing apparatus, where the analog sensor signal has a voltage component which varies according to a condition sensed by the analog sensor, the apparatus comprising:

a first conversion circuit coupled to the analog sensor for receiving the analog sensor signal and for generating an analog information transfer signal having a signal component which varies in relation to the voltage component of the analog sensor signal;

a signal transfer device for transferring the analog information transfer signal to a first audio input of the personal computing apparatus;

a second conversion circuit coupled to the first audio input of the personal computing apparatus for generating a digital information signal based upon the analog information transfer signal having the signal component; and a processor associated with the personal computing apparatus for operating on the digital information signal to generate an information output signal based upon the signal component, where the information output signal varies in relation to the voltage component of the analog sensor signal.

13. The data acquisition apparatus of claim 12 wherein the second conversion circuit comprises a sound card associated with the personal computing apparatus.

14. A data acquisition apparatus for acquiring an analog input signal from an analog sensor, and for generating digital data based on the analog input signal for processing by a personal computing apparatus, where the analog input signal has a voltage component which varies according to a condition sensed by the analog sensor, the apparatus comprising:

a first conversion circuit coupled to the analog sensor for receiving the analog input signal and for generating an analog information transfer signal having a signal component which varies in relation to the voltage component of the analog input signal, wherein the first conversion circuit comprises a voltage-to-frequency converter for generating the analog information transfer signal having a frequency component which varies in relation to the voltage component of the analog input signal;

a signal transfer device for transferring the analog information transfer signal to a first audio input of the personal computing apparatus;

a second conversion circuit coupled to the first audio input of the personal computing apparatus for generating a digital information signal based upon the analog information transfer signal having the signal component; and a processor associated with the personal computing apparatus for operating on the digital information signal to generate an information output signal based upon the signal component, where the information output signal varies in relation to the voltage component of the analog input signal, wherein the processor includes a frequency-to-voltage converter module for operating on the digital information signal to generate the information output signal based upon the frequency component of the analog information transfer signal.

15. A data acquisition apparatus for acquiring an analog input signal from an analog sensor, and for generating digital data based on the analog input signal for processing by a personal computing apparatus, where the analog input signal has a voltage component which varies according to a condition sensed by the analog sensor, the apparatus comprising:

a first conversion circuit coupled to the analog sensor for receiving the analog input signal and for generating an analog information transfer signal having a signal component which varies in relation to the voltage component of the analog input signal;

a signal transfer device for transferring the analog information transfer signal to a first audio input of the personal computing apparatus, the signal transfer device comprising an audio record/playback device operable to be coupled to the first conversion circuit for receiving the analog information transfer signal, the audio record/playback device for recording the analog information transfer signal on a first audio channel, and operable to be coupled to the first audio input of the personal computing apparatus for transferring the analog information transfer signal from the first audio channel to the first analog input of the personal computing apparatus;

a second conversion circuit coupled to the first audio input of the personal computing apparatus for generating a digital information signal based upon the analog information transfer signal having the signal component; and a processor associated with the personal computing apparatus for operating on the digital information signal to generate an information output signal based upon the signal component, where the information output signal varies in relation to the voltage component of the analog input signal.

16. The data acquisition apparatus of claim 15 further comprising:

a microphone for generating an audio input signal, the microphone electrically coupled to a second audio channel of the audio record/playback device;

the audio record/playback device for recording the audio input signal on the second audio channel, and operable to be coupled to a second audio input of the personal computing apparatus for transferring the audio input signal from the second audio channel to the second audio input of the personal computing apparatus.

17. A data acquisition apparatus for acquiring an analog input signal from an analog sensor, and for generating digital data based on the analog input signal for processing by a personal computing apparatus, where the analog input signal has a voltage component which varies according to a condition sensed by the analog sensor, the apparatus comprising:

a first conversion circuit coupled to the analog sensor for receiving the analog input signal and for generating an analog information transfer signal having a signal component which varies in relation to the voltage component of the analog input signal;

a signal transfer device for transferring the analog information transfer signal to a first audio input of the personal computing apparatus;

a second conversion circuit coupled to the first audio input of the personal computing apparatus for generating a digital information signal based upon the analog information transfer signal having the signal component;

a processor associated with the personal computing apparatus for operating on the digital information signal to generate an information output signal based upon the signal component, where the information output signal varies in relation to the voltage component of the analog input signal; and a microphone for generating an audio input signal, the microphone electrically coupled to a second audio input of the personal computing apparatus.

18. A method for acquiring sensor information from an analog sensor and transferring the sensor information to a personal computing apparatus, comprising:

(a) receiving an analog sensor signal from the analog sensor, the analog sensor signal having a voltage component that varies according to the sensor information;

(b) generating an analog information transfer signal having a signal component which varies in relation to the voltage component of the analog sensor signal;

(c) transferring the analog information transfer signal to a first analog audio input of the personal computing apparatus;

(d) generating a digital information signal based upon the analog information transfer signal having the signal component; and (e) operating on the digital information signal to generate an information output signal based upon the signal component, the information output signal thereby varying in relation to the voltage component of the analog sensor signal.

19. The method of claim 18 further comprising:

(f) providing the information output signal to a visual display device; and (g) displaying the information on the visual display device based on the information output signal.

20. The method of claim 18 wherein:

step (b) further comprises generating the analog information transfer signal having an amplitude component that varies in relation to the voltage component of the analog input signal; and step (e) further comprises operating on the digital information signal to generate the information output signal based upon the amplitude component.

21. The method of claim 18 wherein:

step (b) further comprises generating the analog information transfer signal having a frequency component that varies in relation to the voltage component of the analog input signal; and step (e) further comprises operating on the digital information signal to generate the information output signal based upon the frequency component.

* * * * *